United States Patent
Maggiulli

(12) 
(10) Patent No.: US 6,443,932 B1
(45) Date of Patent: Sep. 3, 2002

(54) MULTI-TIERED FEMININE PAD

(76) Inventor: Lori Maggiulli, 235 W. Center St. #1, Covina, CA (US) 91723

(*) Notice: Subject to any disclaimer, the term of this patent is extended or adjusted under 35 U.S.C. 154(b) by 0 days.

(21) Appl. No.: 09/612,039

(22) Filed: Jul. 7, 2000

Related U.S. Application Data

(62) Division of application No. 09/291,699, filed on Apr. 14, 1999, now Pat. No. 6,280,427.

(51) Int. Cl.⁷ .................... A61F 13/15; A61F 13/20

(52) U.S. Cl. .................... 604/385.01; 604/385.14; 604/386

(58) Field of Search .................... 604/385.01, 385.03, 604/385.08, 378, 385.14, 386, 387, 389, 390

(56) References Cited

U.S. PATENT DOCUMENTS

| | | | | |
|---|---|---|---|---|
| 2,929,379 A | * | 3/1960 | Poulsen | 128/290 |
| 3,367,334 A | * | 2/1968 | Testa | 128/290 |
| 4,405,310 A | * | 9/1983 | Karami | 604/383 |
| 4,425,130 A | * | 1/1984 | DesMarais | 604/389 |
| 4,576,597 A | * | 3/1986 | Hlaban | 604/390 |
| 5,429,631 A | * | 7/1995 | Grenier | 604/385.1 |
| 5,599,339 A | * | 2/1997 | Horney | 604/387 |
| 5,720,738 A | * | 2/1998 | Clark | 604/385.1 |
| 5,843,254 A | * | 12/1998 | Clark | 156/66 |
| 5,910,137 A | * | 6/1999 | Clark et al. | 604/387 |

* cited by examiner

Primary Examiner—John G. Weiss
Assistant Examiner—Michele Kidwell
(74) Attorney, Agent, or Firm—Trojan Law Offices

(57) ABSTRACT

A multi-tiered feminine pad consisting of multiple pad layers which have an absorption layer disposed on top of an impermeable material wherein the multiple pad tiers are secured together in a manner which allows removal of successive pad tiers while leaving the remaining pad tiers intact.

5 Claims, 2 Drawing Sheets

MULTI-TIERED FEMININE PAD

This is a divisional of Application Ser. No. 09/291,699, filed Apr. 14, 1999 now U.S. Pat. No. 6,280,427.

FIELD OF THE INVENTION

This invention relates generally to feminine pads, and more specifically to multi-tiered feminine pad.

BACKGROUND OF THE INVENTION

Disposable feminine pads, or sanitary napkins, have long been used by women during their menstrual cycles. Women have also used these feminine pads as an everyday pantyliner to maintain a high level of freshness and cleanliness throughout the day. Such menstrual pads and pantyliners must be replaced periodically. Many enhancements have been made to such products to increase their comfort and the protection they offer, however, for a woman to feel fresh and clean, she must currently replace her feminine pad with an entirely new feminine pad.

The need to replace the feminine pad requires women to carry at least one replacement. Thus, a woman must carry with her some type of receptacle in which to carry her replacement feminine pads. This leaves the woman few options if she wishes to travel without a handbag or purse.

The current art requires that the entire pad must be replaced in order to maintain the highest level of freshness and cleanliness. Hence, the need exists for a feminine pad which will allow a woman to freshen her pad without having to carry along cumbersome replacement pads.

SUMMARY OF THE INVENTION

The present invention is directed toward a feminine pad which satisfies the needs identified above: a feminine pad which can be refreshed without requiring the use of an entirely new replacement pad. The preferred version of this invention includes: i) a first absorbing pad tier consisting of an impermeable layer which is adhered to an undergarment; ii) a first absorbing layer; iii) a first dry weave layer to allow permanent absorption into the absorbing layer without allowing reverse flow of absorbed fluid; iv) a multiplicity of additional pad tiers each consisting of an impermeable layer, an absorbing layer, and a dry weave layer adhered to the immediately lower pad tier but easily removable by perforations along the edges of each pad tier. Alternatively, each pad tier can be adhered by a strip of adhesive with the top pad tier being removed by stripping it away from the next successive tier underneath.

The multi-tiered pad allows the user to attach the pad to an undergarment by using an adhesive strip located on the underside of the pad. When the user wishes to refresh the pad, the top-most tier can be stripped away leaving a clean pad tier underneath. Successive pad tiers can be removed by the user as needed until all tiers have been utilized.

These and other objects and advantages of the present invention will become apparent from the following detailed description of the preferred embodiment of the invention without intending to limit the scope of the invention which is set forth in the appended claims.

DETAILED DESCRIPTION OF THE PREFERRED EMBODIMENT

Figure 1:
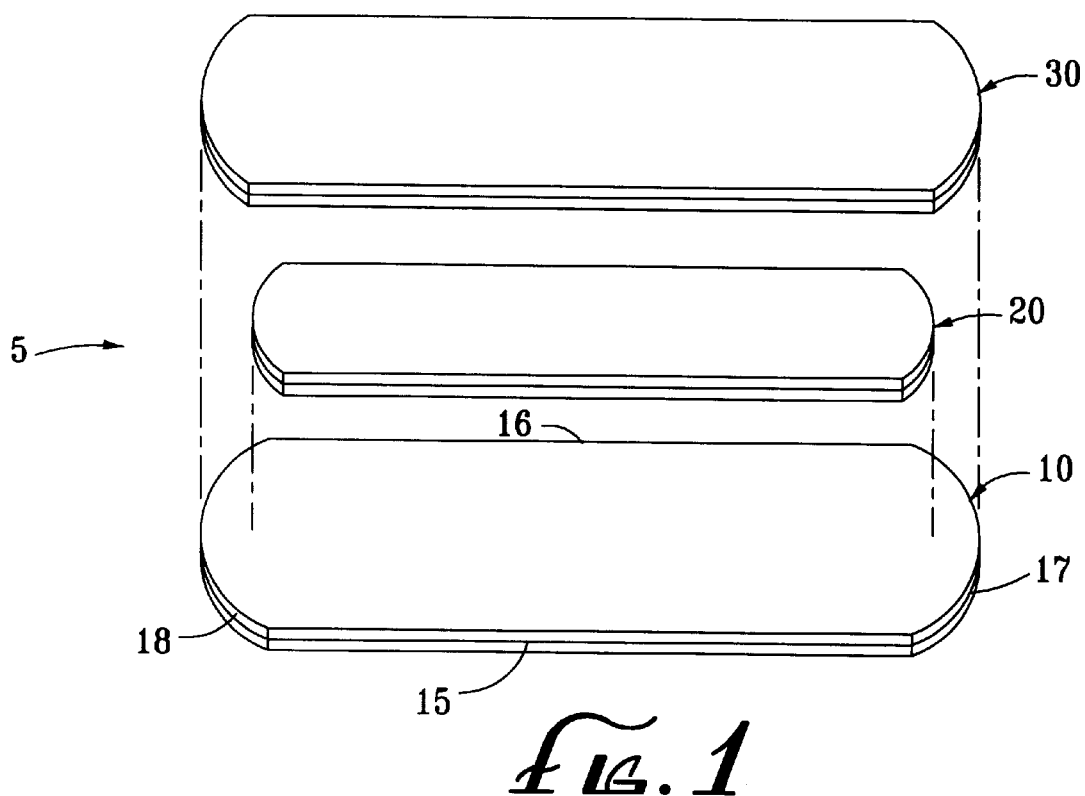
FIG. 1 is an exploded view of the invention.
Figure 2:
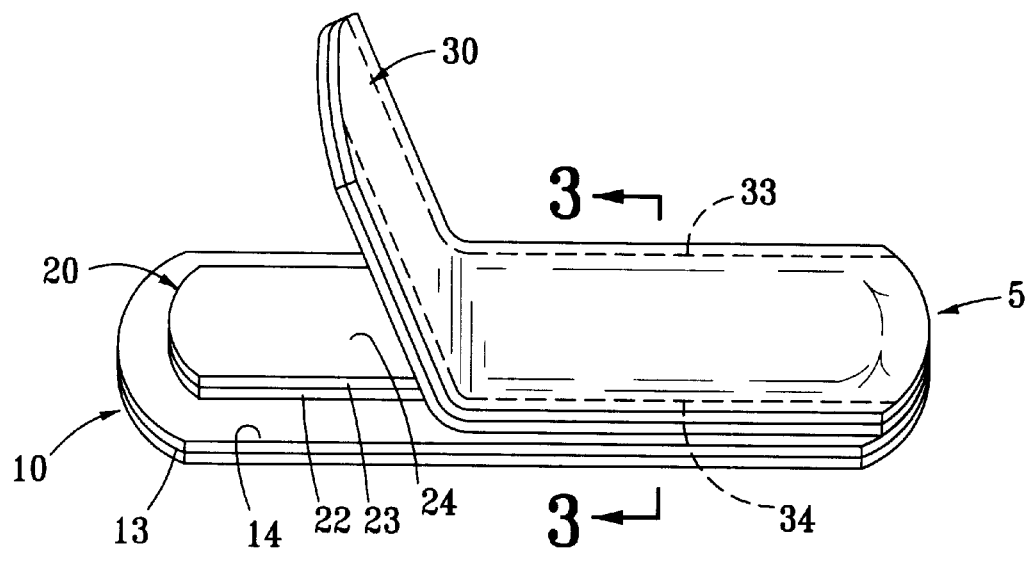
FIG. 2 is an isometric view of the preferred embodiment of the invention in use.

An embodiment of the multi-tiered feminine pad 5 (FIG. 1) includes three pad tiers 10, 20, and 30. The middle tier 20 is smaller than the top tier 30 and the first or bottom tier 10 which are essentially the same size. All three tiers have generally the same shape, opposing elongated sides 15 and 16, and opposing sides that are shorter than the elongated sides, and the shorter sides are rounded 17 and 18. The three tiers are stacked upon each other (FIG. 2).

Figure 3:
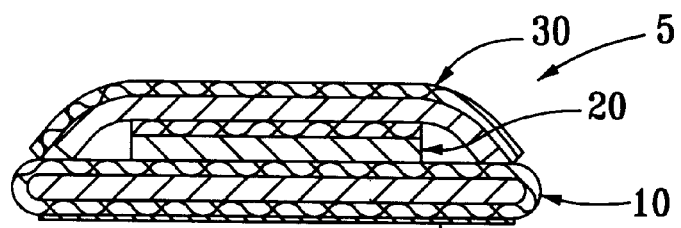
FIG. 3 is a cross-sectional view of the invention in its preferred embodiment.
Figure 4:
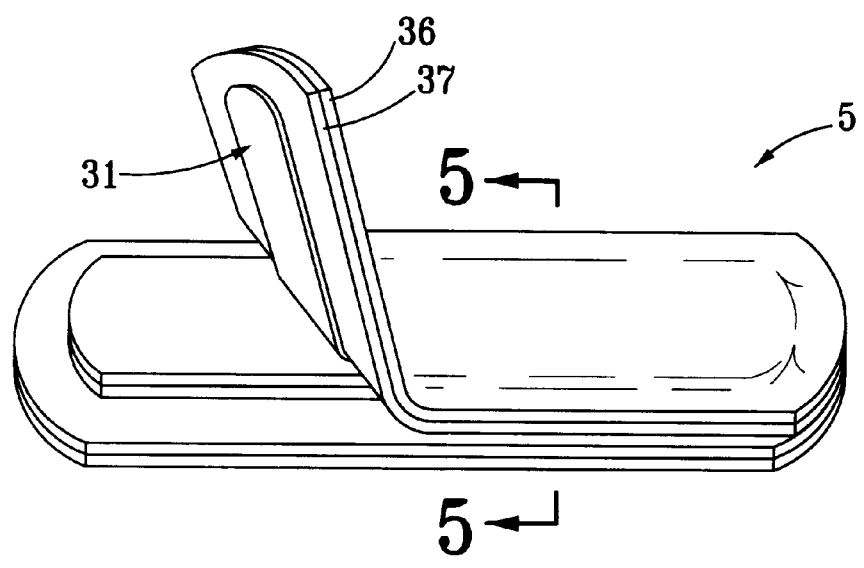
FIG. 4 is an isometric view of an alternative embodiment of the invention in use.

The first pad tier 10 (FIGS. 2 and 3) includes of a layer of impermeable material (not shown), such as plastic, and this layer has an adhesive strip located on the bottom planar surface of the impermeable material to adhere the feminine pad to an undergarment. The adhesive should be of satisfactory strength to securely attach to the undergarment while still allowing the user to remove the pad after use.

Secured to and fitting within the top planar surface of the impermeable material, is an absorbent layer 13 having a top surface and a bottom surface, which comprises a suitably absorbent material. Over the top surface to the absorbent layer is a dry weave material 14 which allows absorption by the absorbent layer, but prevents reverse flow through the dry weave material of the absorbed fluid.

Attached to first pad tier 10 is a middle pad tier 20. The middle pad tier 20 has substantially the same construction as the first pad tier 10, namely, a second impermeable layer 22, a second absorbent layer 23, and disposed on the top planar surface of the absorbent layer is a dry weave material 24. Multiple additional pad tiers having the same construction as the first and second pad tiers can be used.

The multiple pad tiers are secured together by perforations 33 and 34 (FIG. 2) along the first and second elongated sides 15 and 16 of the pad tiers. Successive pad tiers can be removed by tearing along the perforations 33 and 34.

Figure 5:
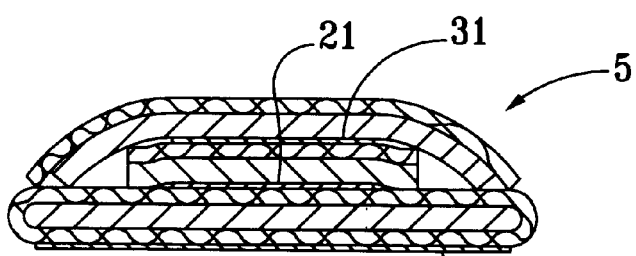
FIG. 5 is a cross-sectional view of the alternative embodiment of the invention.

An alternative embodiment includes securing the first pad tier 10 (FIG. 5) to the middle pad tier 20 with an adhesive strip 21 located on the bottom surface of the impermeable layer. Further, securing the middle tier pad to the top tier pad 30 with an adhesive strip 31 located on the bottom surface of the impermeable layer. The adhesive used should be of suitable strength to keep each pad tier in place when in use, while allowing the user to easily remove pad tiers when necessary.

The spirit and scope of the appended claims should not be limited to the description of the preferred versions contained herein. Although the present invention has been described in considerable detail with reference to certain preferred versions thereof, other versions are possible.

I claim:

1. A multi-tiered feminine pad, which attaches to an undergarment for everyday use as a pantyliner and during a menstrual cycle, comprising:

a first pad tier, a middle pad tier, and a top pad tier;

each pad tier having an under surface, first and second opposing elongated sides, and third and fourth opposing sides that are shorter in length than said first and second sides;

each pad tier further having a plurality of layers, a first layer comprised of an absorbing material, a second layer, having a bottom planar surface and a top planar surface, comprised of an impermeable material; said first layer, having a top surface and a bottom surface, which fits within and is attached to said top planar surface of said second layer;

said top pad tier having a smaller surface area than said first pad tier;

said middle pad tier having a smaller surface area than the top and first pad tiers;

said middle pad tier is located below the top pad tier and above the first pad tier; and means for securing the first pad tier to at least one successive pad tier while allowing for detachment of at least one successive pad tier from the first pad tier, wherein said securing means comprise adhesive disposed along said under surfaces of said pad tiers.

2. A multi-tiered feminine pad as in claim 1 further comprising an adhesive disposed along the bottom planar surface of said impermeable material of said first pad tier for attachment of said multi-tier pad to the undergarment.

3. A multi-tiered feminine pad as in claim 1 wherein third and fourth opposing sides of said pad tiers are rounded.

4. A multi-tiered feminine pad as in claim 1 wherein said impermeable material is plastic.

5. A multi-tiered feminine pad as in claim 1 further comprising a third layer comprised of a material which allows absorption of fluid into said first layers while preventing reverse flow of fluid through the material, wherein the material is disposed over said top surface of said first layers.

* * * * *